Dec. 25, 1956 H. C. SWIM Plant Pat. 1,542
ROSE PLANT
Filed Oct. 12, 1955
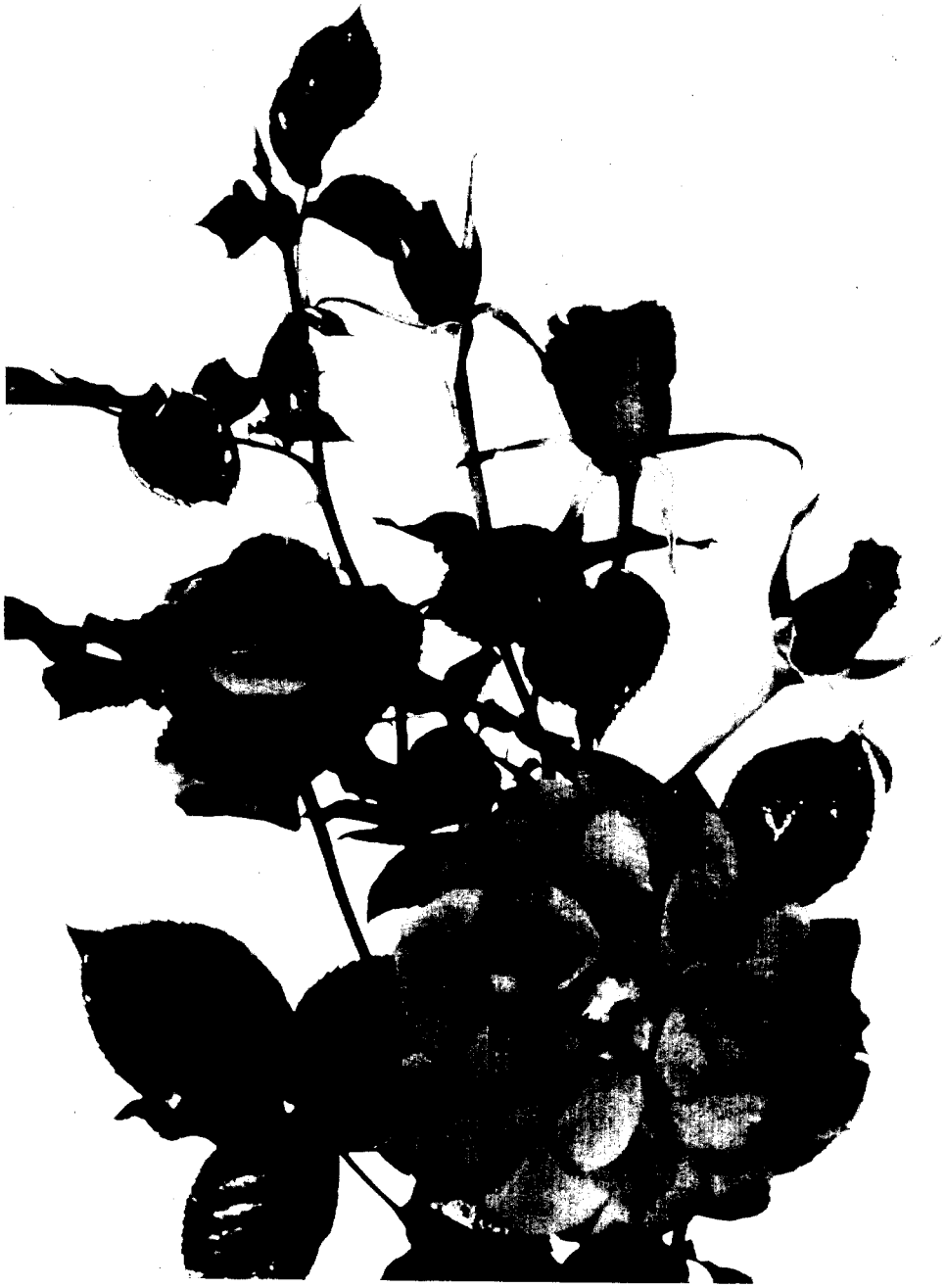
Inventor.
H. C. Swim
By: Robert Cobb
Attorneys.

United States Patent Office

Plant Pat. 1,542
Patented Dec. 25, 1956

1,542

ROSE PLANT

Herbert C. Swim, Ontario, Calif., assignor to Armstrong Nurseries, Inc., Ontario, Calif., a corporation of California Application October 12, 1955, Serial No. 540,177

1 Claim. (Cl. 47—61)

The present invention relates to a new and distinct variety of rose plant of the hybrid tea class, which was originated by me by crossing the variety "Gay Lady" (Plant Patent No. 719) with the variety "Texas Centennial" (Plant Patent No. 162).

The primary objective in making this cross was to produce a new rose variety which combines therein the most desirable characteristics of the two parent varieties. This objective was fully achieved and is evidenced by the following unique combination of characteristics which are predominant in the new variety:

(1) The abundant and glossy foliage which is inherited from the parent variety "Gay Lady";

(2) The abundance of blooms throughout the growing season, as inherited from "Gay Lady";

(3) The habit of bearing the blooms on long and strong flowering stems;

(4) The strong fragrance of the blooms as inherited from the parent variety "Texas Centennial"; and (5) The very dark Red color of the buds and blooms, which is a deeper shade than is found in the buds or blooms of either parent variety.

In comparison with its seed parent, "Gay Lady," the bud and bloom color of the new variety is a very deep shade of Red, whereas the bud and bloom color of "Gay Lady" is only a medium shade of Red; the petal substance of the flower petals of the new variety is substantially better and greater than that of "Gay Lady"; and the blooms of the new variety are borne on longer and stronger flowering stems than those of "Gay Lady."

As compared with its pollen parent, "Texas Centennial," the bud and bloom color of the new variety is much darker than the medium to light shades of Red color, popularly described as Vermilion-Red with some Gold, in the buds and blooms of "Texas Centennial"; the blooms of the new variety are produced in abundance, whereas those of "Texas Centennial" are produced less freely; and the foliage of the new variety is both abundant and glossy, whereas that of "Texas Centennial" is less abundant and non-glossy.

The foregoing characteristics and distinctions definitely differentiate my new variety from its parents, as well as from all other varieties of its class of which I am aware, and asexual reproduction of my new variety by budding, as performed by me at Ontario, California, shows that said characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.
*Seed parent.*—"Gay Lady."
*Pollen parent.*—"Texas Centennial."

Propagation: Holds its distinguishing characteristics through succeeding propagations by budding.

FLOWER

Locality where grown and observed: Ontario, California.

Flowers borne: Usually singly, but sometimes 2 or 3 to stem; on long and strong stems.

Quantity of bloom: Abundant, outdoors.

Continuity: Nearly continuous during growing season.

Fragrance: Strong. Nature—from tea to spicy.

Bud:

*Peduncle.*—From average length to long; from average caliper to heavy; erect; with numerous gland-tipped cilia and few small, soft prickles. Color—near Absinthe Green, Plate XXXI (Ridgway), overlaid with near Deep Corinthian Red, Plate XXVII (Ridgway) on side exposed to the sun.

*Before calyx breaks.*—Size—medium. Form—medium length; pointed; with few gland-tipped cilia on the surface of the bud; usually with slender, much-cut foliaceous parts extending beyond the tip of the bud equal to ¼ or more of its length.

*As calyx breaks.*—Color—between Chrysanthemum Crimson, Plate 824/1, page 169 (Wilson) and Indian Lake, Plate 826/1, page 170 (Wilson).

*Sepals.*—Inner surface with fine, woolly tomentum; margins of alternate sepals lined with fine, woolly tomentum; others lined with gland-tipped cilia and hairs.

*As first petal opens.*—Size—average. Form—medium length; urn-shaped. Color: Outside—between Chrysanthemum Crimson, Plate 824/1, page 169 (Wilson) and Indian Lake, Plate 826, page 170 (Wilson), marked somewhat with near Black, particularly on portion of petal exposed to the sun; inside—near Chrysanthemum Crimson, Plate 824, page 169 (Wilson), with area at base of petal equal to approximately ⅛ of petal near Cardinal Red, Plate 822, page 168 (Wilson), and with exposed portions marked with near Black.

*Opening.*—Opens up well; is not retarded from opening by cold, hot, wet or dry weather.

Bloom:

*Size (when fully open).*—Average; from 3½ inches to 4½ inches.

*Petalage.*—Double; from 23 to 30 petals, plus 4 to 8 petaloids; arranged regularly.

*Form.*—High-centered at first, but becoming open later; petals at first being cupped, with lateral margins of outer petals reflexed usually from ½ to ¾ of petal length and apex sometimes reflexed from ⅛ to ¼ of petal length, with lateral margins of inner petals reflexed ¼ or less of petal length, and apex of inner petals sometimes reflexed ⅛ or less of petal length; becoming later at maturity flat-cupped, with lateral margins usually reflexed from ¾ to the entire length of the petal, and apex sometimes reflexed from ¼ to ½ of petal length.

Petals:

*Texture.*—Medium thickness; leathery; with inside velvety and outside satiny.

*Shape.*—Outside—broadly obovate, with apex flat; sometimes with 1 or 2 notches. Intermediate—obovate, with apex from rounded to flat; sometimes with 1 or 2 notches.—Inside—narrowly obovate; irregular; with apex rounded; with 1 or 2 notches.

This description of a newly opened flower was made from a rose grown outdoors in the month of November, at Ontario, California:

*Color.*—Outer petal: Outside surface—between Cardinal Red, Plate 822/1 page 168 (Wilson) and Chrysanthemum Crimson, Plate 824, page 169 (Wilson), with some markings of near Black on upper portion of petal near margin; inside surface—between Cardinal Red, Plate 822, page 168 (Wilson) and Chrysanthemum Crimson, Plate 824, page 169 (Wilson), marked with near Black on upper portion of petal near margin. Intermediate petal; Outside surface—between Currant Red, Plate 821/2, page 167 (Wilson) and Cardinal Red, Plate 822/1, page 168 (Wilson), marked somewhat near Chrysanthemum Crimson, Plate 824, page 169 (Wilson); inside surface—between Currant Red, Plate 821/1, page 167 (Wilson) and Cardinal Red, Plate 822, page 168 (Wilson), marked with near Chrysanthemum Crimson, Plate 824, page 169 (Wilson), particularly on upper portion of petal near margin. Inner petal: Outside surface—between Currant Red, Plate 821/2, page 167 (Wilson) and Cardinal Red, Plate 822/1, page 168 (Wilson), marked somewhat with near Chrysanthemum Crimson, Plate 824, page 169 (Wilson); inside surface—between Currant Red, Plate 821/1, page 167 (Wilson) and Cardinal Red, Plate 822, page 168 (Wilson), marked with near Chrysanthemum Crimson, Plate 824, page 169 (Wilson) mainly on upper portion of petal near margin.

This description was made from a rose that was open for 3 days outdoors in the month of November, at Ontario, California:

*Color.*—Outer petal: outside surface—near Cardinal Red, Plate 822/1, page 168 (Wilson), with upper portion of petal between Chrysanthemum Crimson, Plate 824, page 169 (Wilson) and Indian Lake, Plate 826, page 170 (Wilson), and with near Black along margins; Inside surface—between Currant Red, Plate 821/2, page 167 (Wilson) and Cardinal Red, Plate 822/1, page 168 (Wilson), with upper portion of petal heavily overlaid with near Chrysanthemum Crimson, Plate 824, page 169 (Wilson). Inner petal: Outside surface—near Cardinal Red, Plate 822/1, page 168 (Wilson) with upper portion of petal between Chrysanthemum Crimson, Plate 824, page 169 (Wilson) and Indian Lake, Plate 826, page 170 (Wilson), and with near Black along margins; inside surface—between Currant Red, Plate 821/2, page 167 (Wilson) and Cardinal Red, Plate 822/1, page 168 (Wilson), with upper portion of petal heavily overlaid with near Chrysanthemum Crimson, Plate 824, page 169 (Wilson).

*General color effect.*—Newly opened flower—between Currant Red, Plate 821, page 167 (Wilson) and Cardinal Red, Plate 822, page 168 (Wilson), marked with near Black toward margins of petals. 3-days open—between Cardinal Red, plate 822, page 168 (Wilson) and Chrysanthemum Crimson, Plate 824/1, page 169 (Wilson), marked somewhat with near Black toward margins of petals.

*Behavior.*—Drop off cleanly; not particularly affected by hot, wet or dry weather.

*Flower longevity.*—On bush in garden—3 or 4 days in November. Cut roses grown outdoors and kept at living-room temperatures—4 days in November.

REPRODUCING ORGANS

Stamens: Average number; arranged regularly about pistils.

Filaments: From short to medium length; from 3 to 7 mm. in length; most with anthers. Color—near Cardinal Red, Plate 822/3, page 168 (Wilson).

Anthers: Large; all open approximately at once. Color: upper side—margins near Carmine, Plate 21/1, page 21 (Wilson), with remainder near Lemon Yellow, Plate 4/2, page 4 (Wilson); under side—margins near Carmine, Plate 21/1, page 21 (Wilson), with remainder near Lemon Yellow, Plate 4/2, page 4 (Wilson).

Pollen: Abundant. Color—near Saffron Yellow, Plate 7/2, page 7 (Wilson).

Pistils: Average number; approximately 75 in number.

Styles: Moderately even; from short to average length; from 4 to 9 mm. in length; average caliper; bunched. Color—lower ½ of style between Uranium Green, Plate 63/3, page 63 (Wilson) and Dresden Yellow, Plate 64/3, page 64 (Wilson); upper ½ of style between Currant Red, Plate 821/3, page 167 (Wilson) and Cardinal Red, Plate 822/3, page 168 (Wilson).

Stigma: Color—near Aureolin, Plate 3/3, page 3 (Wilson).

Ovaries: Most enclosed in calyx, but few protruding from calyx.

Hips: None.

Sepals: Permanent; medium length; recurved. Color: Inside—between Courge Green, Plate XVII (Ridgway) and Biscay Green, Plate XVII (Ridgway), masked by White woolly tomentum; outside—between Courge Green, Plate XVII (Ridgway) and Biscay Green, Plate XVII (Ridgway).

Seeds: None.

PLANT

Foliage:

*Leaves.*—Compound of usually 5 to 7 leaflets; abundant; medium size; leathery; glossy.

*Leaflets.*—Shape—ovoid, with apex acute. Base—round. Margin—simply serrate.

*Color.*—Mature: Upper surface—between Forest Green, Plate XVII (Ridgway) and Dark Dull Yellow-Green, Plate XXXII (Ridgway); under surface—near Chromium Green, Plate XXXII (Ridgway). Young: Upper surface—near Dark Dull Yellow-Green, Plate XXXII (Ridgway), overlaid particularly along margins with near Dark Corinthian Purple, Plate XXXVIII (Ridgway); under surface—near Turtle Green, Plate XXXII (Ridgway), overlaid with near Corinthian Purple, Plate XXXVIII (Ridgway).

*Rachis (the supporting stem of the compound leaf).*—Average size. Upper side—grooved; hairy; some stipitate glands on edges. Under side—prickly; with few stipitate glands.

*Stipules.*—Long; moderately narrow; with short points turning out at an angle of more than 45°.

*Disease resistance.*—Average resistance to mildew, as compared with other varieties grown under comparable cultural conditions at Ontario, California.

Growth:

*Habit.*—Bushy; upright; much-branched.

*Growth.*—Vigorous.

*Canes.*—From medium caliper to heavy.

*Main stems.*—Color—between Spinach Green, Plate V (Ridgway) and Light Elm Green, Plate XVII (Ridgway). Large prickles—many; medium length; almost straight; with moderately long, narrow base. Color—near Light Grayish Olive, Plate XLVI (Ridgway). Small prickles—few. Color—near Light Grayish Olive, Plate XLVI (Ridgway). Hairs—none.

*Branches.*—Color—near Light Elm Green, Plate XVII (Ridgway). Large prickles—many; medium length; almost straight; with moderately long, narrow base. Color—near Sayal Brown, Plate XXIX (Ridgway). Small prickles—few. Color—near Sayal Brown, Plate XXIX (Ridgway). Hairs—none.

*New shoots.*—Color—near Courge Green, Plate XVII (Ridgway), heavily overlaid with between Dark Corinthian Purple, Plate XXXVIII (Ridgway) and Neutral Red, Plate XXXVIII (Ridgway). Large prickles—several; medium length;

almost straight; with moderately long, narrow base. Color—near Corinthian Purple, Plate XXXVIII (Ridgway). Small prickles—few. Color—near Corinthian Purple, Plate XXXVIII (Ridgway). Hairs—none.

I claim:

A new and distinct variety of rose plant of the hybrid tea class, substantially as herein shown and described, characterized particularly as to novelty by its abundant and glossy foliage, the abundance of its blooms throughout the growing season, its habit of bearing blooms on long and strong flowering stems, the strong fragrance of its blooms, and the very dark Red color of its buds and blooms.

No references cited.